(12) United States Patent
Govil

(10) Patent No.: US 11,491,260 B2
(45) Date of Patent: Nov. 8, 2022

(54) METHOD OF MAKING OSTEOINDUCTIVE BONE IMPLANT

(71) Applicant: Bioventus LLC, Durham, NC (US)

(72) Inventor: Amit Prakash Govil, Irvine, CA (US)

(73) Assignee: BIOVENTUS, LLC, Durham, NC (US)

( * ) Notice: Subject to any disclaimer, the term of this patent is extended or adjusted under 35 U.S.C. 154(b) by 0 days.

(21) Appl. No.: 16/459,778

(22) Filed: Jul. 2, 2019

(65) Prior Publication Data
US 2020/0188554 A1 Jun. 18, 2020

Related U.S. Application Data

(63) Continuation of application No. 15/016,072, filed on Feb. 4, 2016, now Pat. No. 10,383,974, which is a
(Continued)

(51) Int. Cl.
*A61L 27/22* (2006.01)
*A61F 2/46* (2006.01)
(Continued)

(52) U.S. Cl.
CPC .............. *A61L 27/227* (2013.01); *A61F 2/28* (2013.01); *A61F 2/4644* (2013.01); *A61K 35/32* (2013.01); *A61L 27/20* (2013.01); *A61L 27/365* (2013.01); *A61L 27/3608* (2013.01); *A61L 27/3687* (2013.01); *A61L 27/3691* (2013.01);
(Continued)

(58) Field of Classification Search
CPC ...... A61L 27/227; A61L 27/20; A61L 27/365; A61L 27/46; A61L 27/54; A61L 27/56; A61L 27/3608; A61L 27/3687; A61L 2400/16; A61L 2430/40; A61L 2300/414; A61L 2300/64; A61K 27/28; A61K 35/32;
(Continued)

(56) References Cited

U.S. PATENT DOCUMENTS

| | | |
|---|---|---|
| 781,882 A | 2/1905 | Hunter |
| 3,458,397 A | 7/1969 | Myers et al. |

(Continued)

FOREIGN PATENT DOCUMENTS

| | | |
|---|---|---|
| CN | 101466415 A | 6/2009 |
| EP | 2374870 B1 | 4/2014 |

(Continued)

OTHER PUBLICATIONS

"Extracellular Matrix Made by Bone Marrow Cells Facilitates Expansion of Marrow-Derived Mesenchymal Progenitor Cells and Prevents Their Differentiation Into Osteoblasts", J Bone Miner Res, Dec. 22(12): 1943-56. (Year: 2007).*

(Continued)

*Primary Examiner* — Carlos A Azpuru
(74) *Attorney, Agent, or Firm* — Barnes & Thornburg LLP

(57) ABSTRACT

Disclosed are various bioactive grafts and methods of making the same. In one embodiment, bone material is harvested from a donor. The harvested bone material is exposed to a lysing agent, the lysing agent configured to release growth factors and bioactive materials from cellular material of the harvested bone material. The harvested bone material is then rinsed with a rinsing agent. The pH of the harvested bone material is substantially neutralized.

6 Claims, 11 Drawing Sheets

Related U.S. Application Data continuation of application No. 12/636,751, filed on Dec. 13, 2009, now abandoned.

(60) Provisional application No. 61/240,283, filed on Sep. 7, 2009, provisional application No. 61/201,612, filed on Dec. 13, 2008.

(51) Int. Cl.

| | | |
|---|---|---|
| *A61L 27/36* | (2006.01) | |
| *A61K 35/32* | (2015.01) | |
| *A61L 27/20* | (2006.01) | |
| *A61L 27/46* | (2006.01) | |
| *A61F 2/28* | (2006.01) | |
| *A61L 27/54* | (2006.01) | |
| *A61L 27/56* | (2006.01) | |

(52) U.S. Cl.
CPC .............. *A61L 27/46* (2013.01); *A61L 27/54* (2013.01); *A61L 27/56* (2013.01); *A61F 2002/2817* (2013.01); *A61F 2002/4646* (2013.01); *A61L 2300/414* (2013.01); *A61L 2300/64* (2013.01); *A61L 2400/16* (2013.01); *A61L 2430/02* (2013.01); *A61L 2430/40* (2013.01)

(58) Field of Classification Search
CPC ...... A61F 2002/2817; A61F 2002/4646; A61F 2/28
See application file for complete search history.

(56) References Cited

U.S. PATENT DOCUMENTS

| | | | |
|---|---|---|---|
| 4,172,128 A | 10/1979 | Thiele et al. | |
| 4,434,094 A | 2/1984 | Seyedin et al. | |
| 4,455,256 A | 6/1984 | Urist | |
| 4,472,840 A | 9/1984 | Jefferies | |
| 4,637,931 A | 1/1987 | Schmitz | |
| 4,652,459 A | 3/1987 | Engelhardt | |
| 4,678,470 A | 7/1987 | Nashef et al. | |
| 4,774,322 A | 9/1988 | Seyedin et al. | |
| 4,902,296 A | 2/1990 | Bolander et al. | |
| 5,073,373 A | 12/1991 | Robert | |
| 5,112,354 A | 5/1992 | Sires | |
| 5,236,456 A | 8/1993 | Robert | |
| 5,275,954 A | 1/1994 | Wolfinbarger et al. | |
| 5,405,390 A | 4/1995 | Robert | |
| 5,455,041 A | 10/1995 | Genco et al. | |
| 5,484,601 A | 1/1996 | Robert | |
| 5,510,396 A | 4/1996 | Prewett et al. | |
| 5,556,379 A | 9/1996 | Wolfinbarger | |
| 5,585,116 A | 12/1996 | Boniface et al. | |
| 5,707,962 A | 1/1998 | Chen et al. | |
| 5,772,994 A | 6/1998 | Ildstad et al. | |
| 5,788,976 A | 8/1998 | Bradford | |
| 5,830,859 A | 11/1998 | Schmidt | |
| 5,854,207 A | 12/1998 | Lee et al. | |
| 5,916,870 A | 6/1999 | Lee et al. | |
| 6,048,964 A | 4/2000 | Lee et al. | |
| 6,049,026 A | 4/2000 | Muschler | |
| 6,090,998 A | 7/2000 | Grooms et al. | |
| 6,189,537 B1 | 2/2001 | Wolfinbarger, Jr. | |
| 6,200,347 B1 | 3/2001 | Anderson et al. | |
| 6,206,923 B1 | 3/2001 | Boyd et al. | |
| 6,293,970 B1 | 9/2001 | Wolfinbarger, Jr et al. | |
| 6,305,379 B1 | 10/2001 | Wolfinbarger, Jr. | |
| 6,432,436 B1 | 8/2002 | Gertzman et al. | |
| 6,436,138 B1 | 8/2002 | Dowd et al. | |
| 6,458,158 B1 | 10/2002 | Anderson et al. | |
| 6,534,095 B1 | 3/2003 | Moore-Smith et al. | |
| 6,544,289 B2 | 4/2003 | Wolfinbarger, Jr et al. | |
| 6,548,080 B1 | 4/2003 | Gertzman et al. | |
| RE38,522 E | 5/2004 | Gertzman et al. | |
| 6,776,800 B2 | 8/2004 | Boyer, II et al. | |
| 6,783,532 B2 | 8/2004 | Steiner et al. | |
| 6,830,763 B2 | 12/2004 | Robert | |
| 6,958,149 B2 | 10/2005 | Vukicevic et al. | |
| 7,019,192 B2 | 3/2006 | Gertzman et al. | |
| 7,026,292 B1 | 4/2006 | Lee et al. | |
| RE39,587 E | 4/2007 | Gertzman et al. | |
| 7,338,757 B2 | 3/2008 | Wolfinbarger, Jr et al. | |
| 7,498,041 B2 | 3/2009 | Masinaei et al. | |
| 7,785,634 B2 | 8/2010 | Borden | |
| 7,811,608 B2 | 10/2010 | Kay et al. | |
| 7,892,577 B2 | 2/2011 | Borden | |
| 7,939,108 B2 | 5/2011 | Morris et al. | |
| 7,977,094 B2 | 7/2011 | Masinaei et al. | |
| 8,002,813 B2 | 8/2011 | Scarborough et al. | |
| 8,137,408 B2 | 3/2012 | Kadiyala et al. | |
| 8,142,991 B2 | 3/2012 | Mills et al. | |
| 8,197,474 B2 | 6/2012 | Scarborough et al. | |
| 8,202,539 B2 | 6/2012 | Behnam et al. | |
| 8,241,673 B2 | 8/2012 | Panasyuk | |
| 8,323,700 B2 | 12/2012 | Morris et al. | |
| 8,328,876 B2 | 12/2012 | Behnam et al. | |
| 8,357,384 B2 | 1/2013 | Behnam et al. | |
| 8,394,419 B2 | 3/2013 | Borden | |
| 8,506,983 B2 | 8/2013 | Mohan et al. | |
| 8,529,962 B2 | 9/2013 | Morris et al. | |
| 8,574,825 B2 | 11/2013 | Shelby et al. | |
| 8,642,061 B2 | 2/2014 | Shimp et al. | |
| 8,669,043 B2 | 3/2014 | Mills et al. | |
| 8,673,019 B2 | 3/2014 | McKay | |
| 8,686,064 B2 | 4/2014 | Shimp et al. | |
| 8,734,525 B2 | 5/2014 | Behnam et al. | |
| 8,740,987 B2 | 6/2014 | Geremakis et al. | |
| 8,753,660 B2 | 6/2014 | Behnam et al. | |
| 8,753,689 B2 | 6/2014 | Morris et al. | |
| 8,758,438 B2 | 6/2014 | Boyce et al. | |
| 8,758,792 B2 | 6/2014 | Behnam et al. | |
| 2001/0020188 A1 | 9/2001 | Sander | |
| 2001/0041792 A1 | 11/2001 | Donda et al. | |
| 2002/0061328 A1* | 5/2002 | Gertzman | A61L 31/005 424/428 |
| 2002/0146401 A1 | 10/2002 | Bell et al. | |
| 2003/0008328 A1 | 1/2003 | Wironen et al. | |
| 2003/0012821 A1 | 1/2003 | Robert | |
| 2003/0039676 A1 | 2/2003 | Boyce et al. | |
| 2003/0206937 A1 | 11/2003 | Gertzman et al. | |
| 2005/0079200 A1 | 4/2005 | Rathenow et al. | |
| 2005/0251268 A1 | 11/2005 | Truncale | |
| 2007/0154563 A1* | 7/2007 | Behnam | A61P 19/10 424/549 |
| 2007/0154653 A1* | 7/2007 | Sawatari | G02F 1/141 428/1.1 |
| 2007/0172433 A1 | 7/2007 | Roveri | |
| 2007/0202148 A1 | 8/2007 | Ringeisen et al. | |
| 2007/0254042 A1 | 11/2007 | Drapeau et al. | |
| 2008/0114465 A1 | 5/2008 | Zanella et al. | |
| 2008/0262633 A1 | 10/2008 | Williams et al. | |
| 2009/0226534 A1 | 9/2009 | Marchosky | |
| 2009/0246244 A1 | 10/2009 | McKay et al. | |
| 2010/0152863 A1 | 6/2010 | Govil | |
| 2010/0159022 A1 | 6/2010 | Pedrozo et al. | |
| 2010/0215673 A1 | 8/2010 | Fan | |
| 2010/0215718 A1 | 8/2010 | Swords et al. | |
| 2010/0310625 A1 | 12/2010 | Fan et al. | |
| 2011/0070312 A1 | 3/2011 | Wei et al. | |
| 2011/0104299 A1 | 5/2011 | Borden | |
| 2011/0195052 A1 | 8/2011 | Behnam et al. | |
| 2011/0274668 A1 | 11/2011 | Scarborough et al. | |
| 2012/0009230 A1 | 1/2012 | Drapeau et al. | |
| 2012/0053692 A1 | 3/2012 | Voor et al. | |
| 2012/0100225 A1 | 4/2012 | McKay | |
| 2012/0251609 A1 | 10/2012 | Huang et al. | |
| 2012/0258178 A1 | 10/2012 | Benham et al. | |
| 2013/0316012 A1 | 11/2013 | Gaskins et al. | |
| 2014/0010890 A1 | 1/2014 | Borden | |
| 2014/0148387 A1 | 5/2014 | Nagaya et al. | |

(56) References Cited

U.S. PATENT DOCUMENTS

| | | | |
|---|---|---|---|
| 2014/0170232 A1 | 6/2014 | Shelby et al. | |
| 2014/0200182 A1 | 7/2014 | Ron | |
| 2016/0151537 A1* | 6/2016 | Govil | A61F 2/4644 |
| | | | 424/549 |

FOREIGN PATENT DOCUMENTS

| | | |
|---|---|---|
| KR | 100754814 B1 | 9/2007 |
| WO | 1995019797 A1 | 7/1995 |
| WO | 2000050102 A1 | 8/2000 |
| WO | 2001000792 A1 | 1/2001 |
| WO | 2003051240 A2 | 6/2003 |
| WO | 2005042048 A2 | 5/2005 |
| WO | 2008150508 A1 | 12/2008 |

OTHER PUBLICATIONS

Ahmadi et al., "Biocompatibility and Gelation of Chitosan-Glycerol Phosphate Hydrogels," Journal of Biomedical Materials Research, Part A, vol. 86, No. 3, (2008), pp. 824-832.

Chen et al., "Extracellular Matrix Made by Bone Marrow Cells Facilitates Expansion of Marrow-Derived Mesenchymal Progenitor Cells and Prevents Their Differentiation into Osteoblasts," J. Bone Miner. Res., vol. 22, No. 12, (2007), pp. 1943-1956.

Chen et al., "Activation of Demineralized Bone Matrix by Genetically Engineered Human Bone Morphogenetic Protein-2 with a Collagen Binding Domain Derived from von Willebrand Factor Propolypeptide," Journal of Biomedical Materials Research, Part A, 80.2 (2007), pp. 428-434.

Chesnutt et al., "Design and Characterization of a Novel Chitosan-Nanocrystalline Calcium Phosphate Composite Scaffold for Bone Regeneration," J. of Biomed. Mater. Res., Part A, vol. 88A, No. 2, (2007), pp. 491-502.

Couto et al., "Development of Bioactive and Biodegradable Chitosan-Based Injectable Systems Containing Bioactive Glass Nanoparticles," Acta Biomaterialia, vol. 5, (2009), pp. 115-123.

Heinemann et al., "In Vitro Evaluation of Textile Chitosan Scaffolds for Tissue Engineering using Human Bone Marrow Stromal Cells," Biomacromolecules, vol. 10, (2009), pp. 1305-1310.

Jing et al., "A Preliminary Study of High Viscous Chitosan/Glycerol Phosphate iwth Demineralized Bone Matrix to Repair Cartilage Defects in Rabbits," Chinese Journal of Reparative and Reconstructive Surgery, vol. 22, No. 12, (2008), pp. 1491-1494.

Kirk et al., "Extracellular Matrix Synthesized by Clonal Osteogenic Cells in Osteoinductive in vivo and in vitro: Role of Transforming Growth Factor-Betal in Osteoblast Cell-Matrix Interaction," Journal of Bone and Mineral Research, vol. 10, No. 8, (1995), pp. 1203-1208.

Lee et al., "The Bone Regenerative Effect of Platelet-Derived Growth Factor-BB Delivered with a Chitosan/Tricalcium Phosphate Sponge Carrier," J. Periodontol, vol. 71, No. 3, (2000), pp. 418-424.

Lin et al., "The Effect of Crosslinking Heparin to Demineralized Bone Matrix on Mechanical Strength and Specific Binding to Human Bone Morphogenetic Protein-2," Biomaterials, vol. 29, (2008), pp. 1189-1197.

Ma et al., "A Study on the Effect of the Chitosan Thermosensitive Hydrogel Loading Recombinant Human Bone Morphogenetic Protein-2 on Repairing Periodontal Defects," West China Journal of Stomatology, vol. 26, No. 1, (2008), pp. 23-26.

Muzzarelli, "Chitins and Chitosans for the Repair of Wounded Skin, Nerve, Cartilage and Bone," Carbohydrate Polymers, vol. 76, (2009), pp. 167-182.

Sakurai, "Purification of Bone Morphogenetic Protein and Investigation of its Effects on Osteoblastic Cell Line UMR108," The Journal of Stomatological Society, vol. 60, No. 1, (1993), pp. 169-182.

Thein-Han et al., "Chitosan as Scaffold Matrix for Tissue Engineering," Materials Science and Technology, vol. 24, No. 9, (2008), pp. 1062-1075.

Raval et al., "Osteoinductive Ability of Confuent Saoa-2 Cells Correlates with Enhanced Expression of Bone Morphogenic Proteins," Journal of Orthopaedic Research, vol. 14, No. 4, (1996), pp. 605-610.

Russell et al., "Clinical Utility of Demineralized Bone Matrix for Osseous Defects, Arthrodesis, and Reconstruction mpact of Processing Techniques and Study Methodology," Orthopedics, vol. 22, No. 5, (1999), pp. 524-531.

Thein-Han et al., "Biomimetic Chitosan-Nanohydroxyapatite Composite Scaffolds for Bone Tissue Engineering," Acta Biomaterialia, vol. 5, (2009), pp. 1182-1197, available online Dec. 10, 2008.

Tziafas et al., "Inductive Influences of Demineralized Dentin and Bone Matrix on Pulp Cells: An Approach of Secondary Dentinogenesis," J. Dent. Res , vol. 69, No. 1, (1990), pp. 75-81.

Urist et al., "Inductive Substrates for Bone Formation," Clinical Orthopaedics and Related Research, No. 59, (1968), pp. 59-96.

Urist et al., "The Bone Induction Principle," Clinical Orthopaedics and Related Research, No. 53, (1967), pp. 243-283.

Wahl, "Collagen-Hydroxyapatite Composites for Hard Tissue Repair," European Cells and Materials, vol. 11, (2006), op. 43-56.

Wolfinbager Jr, et al., "Demineralized Bone Matrix: Maximizing New Bone Formation for Successful Bone Implantation", Orthopedic Biology and Medicine: Musculoskeletal Regeneration, Biological Materials and Methods, 2008.

Extended Search Report, issued in EP Application No. 09832666.3, dated Apr. 26, 2013.

Extended Search Report, issued in EP Application No. 10836450.6, dated Apr. 4, 2013.

First Examination Report, issued in AU Application No. 2009324417, dated Jun. 26, 2013.

First Examination Report, issued in AU Application No. 2010328427, dated May 13, 2013.

First Office Action, issued in CN Application No. 200980155596.X, dated Apr. 15, 2013.

First Office Action, issued in CN Application No. 201080063724.0, dated Dec. 12, 2013.

International Preliminary Report on Patentability, issued in PCTUS2009067799, dated Jun. 14, 2011.

International Search Report, issued in PCTUS2009067799, dated Sep. 27, 2010.

International Search Report, issued in PCTUS2010058876, dated Aug. 25, 2011.

Search Report, issued in CN Application No. 201080063724.0, dated Dec. 4, 2013.

Second Examination Report, issued in AU Application No. 2009324417, dated Feb. 21, 2014.

Second Examination Report, issued in AU Application No. 2010328427, dated Dec. 17, 2013.

Second Office Action, issued in CN Application No. 200980155596.X, dated Sep. 11, 2013.

Second Office Action, issued in CN Application No. 201080063724.0, dated Jul. 10, 2014.

Supplementary Search Report, issued in EP Application No. 09832666.3, dated Apr. 17, 2013.

Office Action, issued in JP Application No. 2016-077958, dated Dec. 20, 2016.

Office Action, issued in AU Application No. 2014218483, dated Dec. 24, 2015.

Third Office Action, issued in CN Application No. 200980155596.X, dated Dec. 23, 2013.

Office Action, issued in AU Application No. 2014218483, dated Oct. 25, 2016.

Office Action, issued in EP Application No. 09832666.3, dated Jun. 7, 2016.

Office Action, issued in EP Application No. 10836450.6 dated Apr. 23, 2015.

Office Action, issued in BR Application No. 112012014263-1 dated Mar. 20, 2018.

Office Action, issued in KR Application No. 10-2011-7016270 dated May 24, 2016.

Office Action, issued in CN Application No. 12015082001713450 dated Aug. 25, 2015.

(56) References Cited

OTHER PUBLICATIONS

Office Action, issued in AU Application No. 2014259553 dated Apr. 27, 2015.
Office Action, issued in AU Application No. 2016213839 dated Nov. 29, 2016.

* cited by examiner

METHOD OF MAKING OSTEOINDUCTIVE BONE IMPLANT

CROSS-REFERENCE TO RELATED APPLICATIONS

This application is a continuation of U.S. patent application Ser. No. 15/016,072, filed Feb. 4, 2016, the contents of which is hereby incorporated herein in its entirety. U.S. application Ser. No. 15/016,072, is a continuation of U.S. application Ser. No. 12/636,751, filed Dec. 13, 2009, which claims the benefit of U.S. Provisional Application Ser. No. 61/201,612 entitled "STIMULATIVE GROWTH AGENTS DERIVED FROM PHYSIOLOGICAL FLUIDS AND METHOD OF MAKING," filed Dec. 13, 2008, both of which are incorporated by reference herein in their entirety. U.S. patent application Ser. No. 12/636,751 also claims the benefit of U.S. Provisional Application Ser. No. 61/240,283 entitled "BIOACTIVE ALLOGRAFTS AND COMPOSITES," filed Sep. 7, 2009, which is incorporated herein in its entirety.

BACKGROUND

Bone grafts, whether an allograft, autograft or xenograft can be employed in patients suffering from painful or otherwise abnormal conditions related to instabilities or abnormalities in the skeletal structure. As a non-limiting example, a patients suffering from a spinal instability or excess movement of one or more vertebrae may be treated with a spinal fusion procedure involving removal of a portion of an intervertebral disc located between two vertebrae. A bone graft or spinal implant or a combination of both can then be inserted into or around the area of removed intervertebral disc to facilitate the fusion of two adjacent vertebrae. Such bone grafts or spinal implants can comprise harvested bone fragments made of cortical, cancellous, corticocancellous or a combination of all three aforementioned types of bone material. Patients may also suffer from various degenerative conditions for which implantation of a bone graft can be chosen as a treatment.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the disclosure. Moreover, in the drawings, like reference numerals designate corresponding parts throughout the several views.

DETAILED DESCRIPTION

Figure 1:
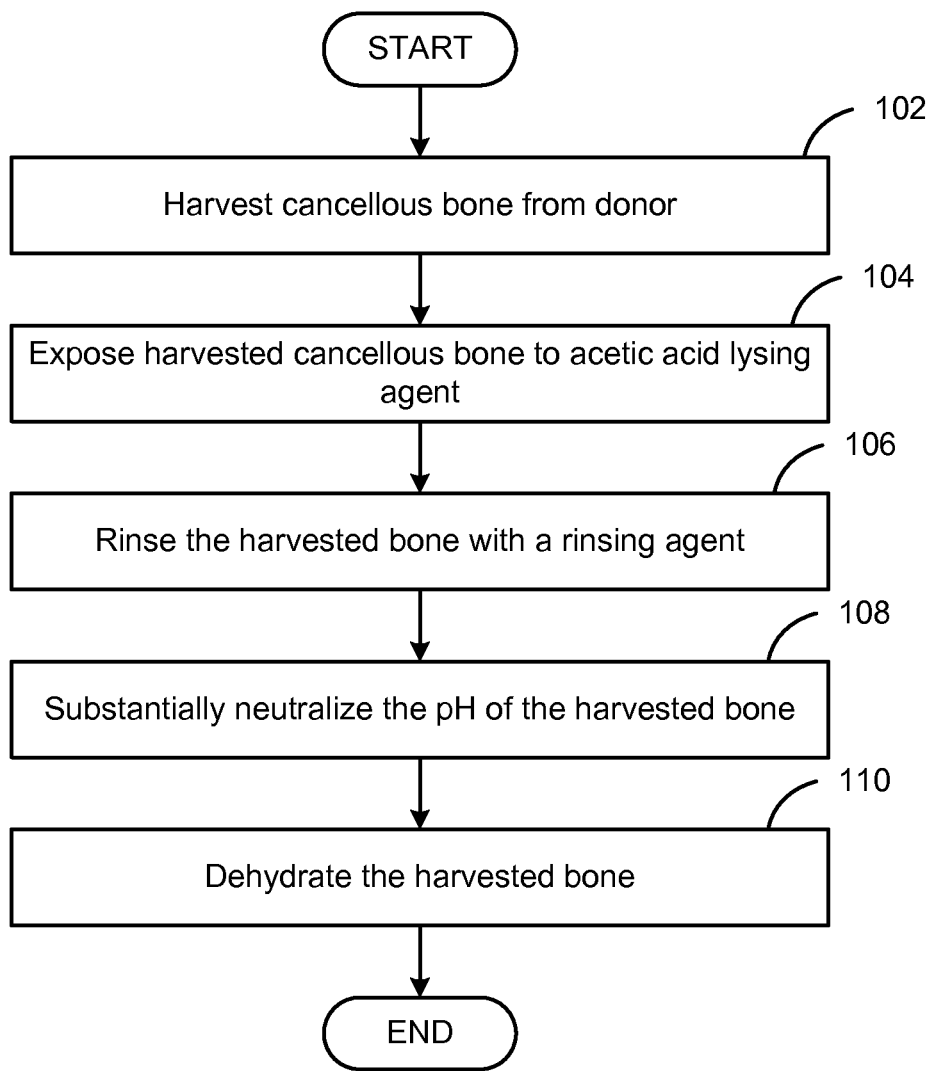
FIG. 1 is a flow diagram illustrating one embodiment in accordance with the present disclosure.

Various embodiments of the present disclosure relate to bioactive factors that stimulate tissue growth. As can be appreciated these bioactive factors can be derived from physiological solutions containing cells. Physiological solutions may exist as solutions naturally in the body or be derived from tissue when the cells are extracted. Any tissue containing cells may be a source of physiological fluid, such as, for example, mesodermal, endodermal, and ectodermal tissues. Examples of these tissues include bone marrow, blood, adipose, skin, muscle, vasculature, cartilage, ligament, tendon, fascia, pericardium, nerve, and hair. These tissues may also include organs such as the pancreas, heart, kidney, liver, intestine, stomach, and bone. The cells may be concentrated prior to processing by the current invention.

One embodiment of the present disclosure relates to osteoinductive implants made from cellular bone tissue as well as methods of making osteoinductive implants. Implants made from cellular bone tissue can include osteoinductive and/or osteoconductive materials to facilitate fusion and/or new bone growth in or around an area of implant insertion. Accordingly, in accordance with one embodiment, a portion of cancellous, corticocancellos and/or cortical bone or any combination thereof can be harvested from a donor. In one embodiment, the harvested material can be harvested in such a way as to retain as much bone marrow in the harvested sample as possible.

The harvested sample can be exposed to lysing conditions and/or a lysing agent to facilitate lysis of the cells therein to release growth factors and nutrients contained sample. In other words, the harvested sample can be exposed to a lysing agent that lyses the cells within the harvested sample. Once cellular components are lysed, they release growth factors and/or bioactive materials, such as cytokines and nutrients, to stimulate growth, differentiation, and repair. These growth agents can be cytokines such as proteins, hormones, or glycoproteins including members of the TGF-β family (including bone morphogenetic proteins), interleukins, interferons, lymphokines, chemokines, platelet derived growth factors, VEGF, and other stimulative agents that promote growth, repair or regenerate tissues.

In other embodiments, cells from other tissues can be lysed to release growth agents that can be binded to the harvested sample and further processed as an implant. Lysing conditions may be mechanical in nature such as thermolysis, microfluidics, ultrasonics, electric shock, milling, beadbeating, homogenization, french press, impingement, excessive shear, pressure, vacuum forces, and combinations thereof. Excessive shear may be induced by aggressive pipetting through a small aperture, centrifuging at excessive revolutions per minute resulting in high gravity forces. Rapid changes in temperature, pressure, or flow may also be used to lyse cellular components. Lysing conditions can include thermolysis techniques that may involve freezing, freeze-thaw cycles, and heating to disrupt cell walls. Lysing conditions can also include microfluidic techniques that may involve osmotic shock techniques of cytolysis or crenation.

Lysing conditions can also include the imposition of ultrasonic techniques, including, but not limited to, sonication, sonoporation, sonochemistry, sonoluminescence, and sonic cavitation. Lysing conditions can also include electric shock techniques such as electroporation and exposure to high voltage and/or amperage sources. Lysing conditions can further include milling or beat beating techniques that physically collide or grind cells in order to break the cell membranes, releasing the stimulative agents contained within.

Lysing can also be accomplished by exposing cells of the harvested sample to a lysing agent, which can facilitate release of stimulative growth agents include lysis due to pH imbalance, exposure to detergents, enzymes, viruses, solvents, surfactants, hemolysins, and combinations thereof. Chemical induced lysis of the cells by pH imbalance may involve exposure of cells of the harvested sample to a lysing agent in order to disrupt the cell walls and release soluble growth agents. In some embodiments, a lysing agent can include one or more acids and/or bases.

After exposure to the lysing agent, the harvested sample may be exposed to buffers or other solutions to substantially neutralize the pH of the mixture of the growth factors and the lysing agent. In some embodiments, it may be desired that the pH be acidic (e.g., pH below 7) or basic (e.g., pH above 7) to retain solubility of particular growth factors or bioactive agents. For example, bone morphogenetic proteins (particularly BMP-2, BMP-4, BMP-6, BMP-7, BMP-9, BMP-14, and other bone morphogenetic proteins 1-30) are more soluble at acid pH values under 7 than neutral or basic pH.

In other embodiments, a lysing agent can include a volatile acid or base, such as acetic acid or ammonia, and the cellular material, after exposure to the lysing agent, may be neutralized or partially neutralized by drying techniques such as evaporation, vacuum drying, lyophilization, freeze drying, sublimation, precipitation, and similar processes as can be appreciated. In yet other embodiments, a lysing agent can include detergents that can disrupt cell walls and remove any lipid barriers that may surround the cell. Enzymes, viruses, solvents, surfactants, and hemolysins can also help cleave or remove outer cell membranes releasing the bioactive growth agents contained within.

The use of these lysing agents and/or exposure of the harvested sample to lysing conditions may be followed by neutralization, as noted above, and/or another secondary process to remove any undesired remnants. The growth agents, nutrients, etc., released by the lysing process may be added to a carrier such as a synthetic scaffold, biologic scaffold, and autologous, allogeneic, and xenograft tissue. In yet other embodiments, a harvested sample acting as a carrier can be exposed to lysing conditions and/or a lysing agent, and growth factors released by the lysing process can be binded to at least a portion of the sample. In other words, the growth agents released by lysing of cellular material may be used immediately for autologous use. In other embodiments, the released growth agents may be stored for allogenic use. Storage techniques can include freezing or lyophilization to preserve bioactivity. The growth factors and nutrients may also be frozen or lyophilized on the chosen carrier to allow for complete binding of the stimulative agent to the carrier and to allow for immediate use by the surgeon. Lyophilization also allows for greater room temperature shelf life and an opportunity for concentration into a smaller volume.

Another embodiment of the present invention relates to obtaining a specific set of growth factors and nutrients from a physiological solution containing cells. In this embodiment, cells are lysed as described above and the lysate solution is subjected to materials with a charged surface, including, but not limited to, chromatography resins, ceramics, mineralized tissues, demineralized tissues, soft tissues, and other materials with an electric charge. The charged surface attracts certain stimulative growth agents and molecules removing them from the lysate solution. The remaining growth agents can then be used to regenerate or repair the desired tissue type. Similar to the previous embodiment, the growth agent solution can be further concentrated and frozen or lyophilized in order to extend shelf life.

Another embodiment of the disclosure includes selectively rinsing, lysing, or removal of certain cellular components while retaining other cellular components. Selective lysing or removal can be accomplished physically by methods described above. As can be appreciated, certain cells can be resistant to various lysing mechanisms. As a non-limiting example, mesenchymal stem cells (MSC) are resistant to cytolysis and osmotic lysis due to their resistant cell walls and ineffective cells volumes. Accordingly, to accomplish selective lysing, osmotic lysis can be used to lyse red and white blood cells from blood or bone marrow. Once the non-resistant cells are lysed, the resulting solution is an enriched MSC population. The solution can then be further concentrated via centrifugation, florescence-activated cell sorting (FACS), filtration, magnetic bead selection and depletion, and/or gravity sedimentation. For allogeneic transplantation, FACS and magnetic bead separation and depletion can be useful in removing any remaining cells that would cause an immune response from the implant patient. Once implanted, cells can function in a homologous manner and differentiate in the desired phenotype.

Another embodiment of the disclosure includes a combination of previous two embodiments. A physiological solution may be enriched by selective lysis and further concentrated by centrifugation, FACS, magnetic bead selection and depletion, and/or gravity sedimentation. The enriched physiological solution is added to a physiological solution that has been lysed in the methods described previously in order to help induce differentiation of the cells into the desired phenotype. These cells can then function in the desired manner to regenerate and repair tissues.

In another embodiment, cancellous bone may be exposed to a weak lysing agent (such as less than 1M acetic acid) that only partially lyses the cell population present. In this embodiment, the partial lysis releases growth factors and binds them to the bone while other cells, such as mesenchymal stem cells and progenitor cells, may still remain viable and attached to the bone.

In another embodiment, cancellous bone may be exposed a weak lysing agent (such as water) and then subjected to mechanical lysing conditions previously stated (such as thermolysis, high/low pressure, sonication, centrifugation, etc.). Once the cells have lysed, the bone, cell fragments, and debris are removed from the solution containing the growth factors. The solution may then become positively charged by the addition of an acid or another proton donor fluid. The growth factors in the solution may then be further concentrated using techniques described, frozen, or lyophilized into a soluble powder. The soluble powder could be reconstituted with a fluid prior adding it to an implant during surgery or added in the dry powder form to an implant prior to implantation.

In another embodiment, an osteoinductive growth factor can be formed from physiological fluids containing cells. These cells are lysed as previously described and may be loaded onto allograft bone from the same tissue donor as the cells. The stimulative growth agents may be loaded onto the bone prior to lyophilization or freezing. The bone may be mineralized or demineralized prior to loading of the stimulative growth agents to allow for more complete bonding of the stimulative growth agents. The bone may also be morselized prior to or after loading with stimulative growth agents allowing it to be used in a flowable composition.

In another embodiment, a physiological fluid containing cells, such as synovial fluid, may be harvested from a live donor, cadaveric donor, or autologously. The fluid may be subjected to mechanical or chemical lysing conditions described in order to solubilize growth factors. Once the growth factors are released from the cells, the solid materials (such as cells fragments, debris, or platelets) may be removed by processes described such as filtration, centrifugation, or gravity sedimentation. Once the solid materials are removed, the solution may be then become positively charged by the addition of an acid or another proton donor fluid. The growth factors in the solution may then be further concentrated using techniques described, frozen, or lyophilized into a soluble powder. The soluble powder could be reconstituted with a fluid prior adding it to an implant during surgery or added in the dry powder form to an implant prior to implantation. Alternatively, cartilage with or without synovial fluid can be prepared in a similar fashion for the repair and regeneration of cartilage or spinal discs. In addition, other tissues such as muscle, adipose, nerve, dermis, cardiac tissue, vascular tissue, nucleus pulposus tissue, annulus fibrosus tissue, or other solid tissues can be prepared in this fashion to be used to help repair or regenerate tissues.

Stimulative growth agents can be derived from various cellular solutions. These solutions may comprise cultured and/or uncultured cells, and can be autologous, allogeneic, or xenogeneic in origin. If the cells are allogeneic or xenogeneic in origin, at least partial lysing or immune cells depletion by methods previously described can be performed so that the stimulative growth agents do not elicit an immune response in the patient. Alternatively, immune response agents, such as CD45+ cells and other leukocytes, may be removed prior to use to reduce or eliminate immune response. These immune response agents may be removed by the selective lysing as previously described in this disclosure.

The systems and methods described herein can be employed in surgical environments where the implantation of stimulative growth agents in a patient is desired. Although the present disclosure describes the methods and systems for producing stimulative growth agents, particularly ones derived from physiological fluids containing cells or cellular tissues, it is understood that the methods and systems can be applied for a wide variety of medical applications including ones directed at regeneration or repair of bone, cartilage, muscle, tendon, ligament, vasculature, fat, annulus fibrosus, nucleus pulposus, skin, hair, blood, lymph nodes, fascia, neural, cardiac, pancreatic, hepatic, ocular, dental, digestive, respiratory, reproductive, and other soft tissue applications, such as in regenerative medicine and tissue engineering.

Reference is now made to FIG. 1, which depicts a method in accordance with one embodiment of the disclosure. In the embodiment illustrated in FIG. 1, an implant that can be suitable for bone applications is shown. In the embodiment of FIG. 1, cancellous bone is recovered from a cadaver, live donor, or harvested autologously from a patient in box 102. The harvested cancellous bone can be ground or cut to a desired shape and configuration as can be appreciated. Care may be taken to retain some cellular material, bone marrow, and/or blood within the bone during harvest and cutting operations. In prior art implants, bone marrow and/or blood within the bone can be systematically removed and/or cleaned from the harvested bone sample. In an embodiment of the disclosure, cancellous bone may have cortical bone portions such as in the iliac crest, vertebral bodies, chondyles, etc. Accordingly, in some embodiments, depending on the needs of a particular application, the cancellous bone may have cortical portions removed prior to further processing.

The cancellous bone is then exposed to acetic acid in box 104, which acts as a lysing agent as described above. In one embodiment, the acetic acid concentration can be greater than 1%, in a molarity range of 0.2M-17M. The acetic acid lysing agent is employed to lyse cells remaining in the porous bone structure and on bone surface of the cancellous bone. The lysing of the cells releases and solubilizes growth factors and bioactive materials contained in the cellular material. The acetic acid lysing agent also allows the solubilized bioactives to bind to the bone. The bone may be further rinsed and cleaned by a rinsing agent in box 106 after exposure to the acetic lysing agent and after growth factors and/or bioactive materials bind to the bone. Rinsing can be conducted in order to remove excess acetic acid, cell fragments, lipids, and/or debris. Additionally, pH of the harvested bone may be substantially neutralized in box 108. In some embodiments, the pH of the harvested bone can be neutralized by the rinsing agent and rinsing step in box 106. In other embodiments, pH neutralization may not be required. Further pH neutralization of the harvested bone may be accomplished by dehydrating in box 110 by evaporation, vacuum drying, or lyophilization to reduce the acetic acid lysing agent to a residue and bring the implant to a more neutral pH.

Rinsing solutions can be water, saline (NaCl, PBS, etc.), peroxides, alcohol (isopropyl, ethanol, etc.), crystalloids, sterilizing fluids (antibiotics such as gentamicin, vancomycin, bacitracin, polymixin, amphotericin, ampicillin, amikacin, teicoplanin, etc.), preserving fluids (DMEM, DMSO, mannitol, sucrose, glucose, etc.), storage agents, and/or other fluids used in processing of allografts. The resulting product yields a cancellous bone implant with increased bioactivity. In some embodiments, ground particulate filler implants as well as structural cancellous bone implants with increased bioactivity may be formed.

Figure 2:
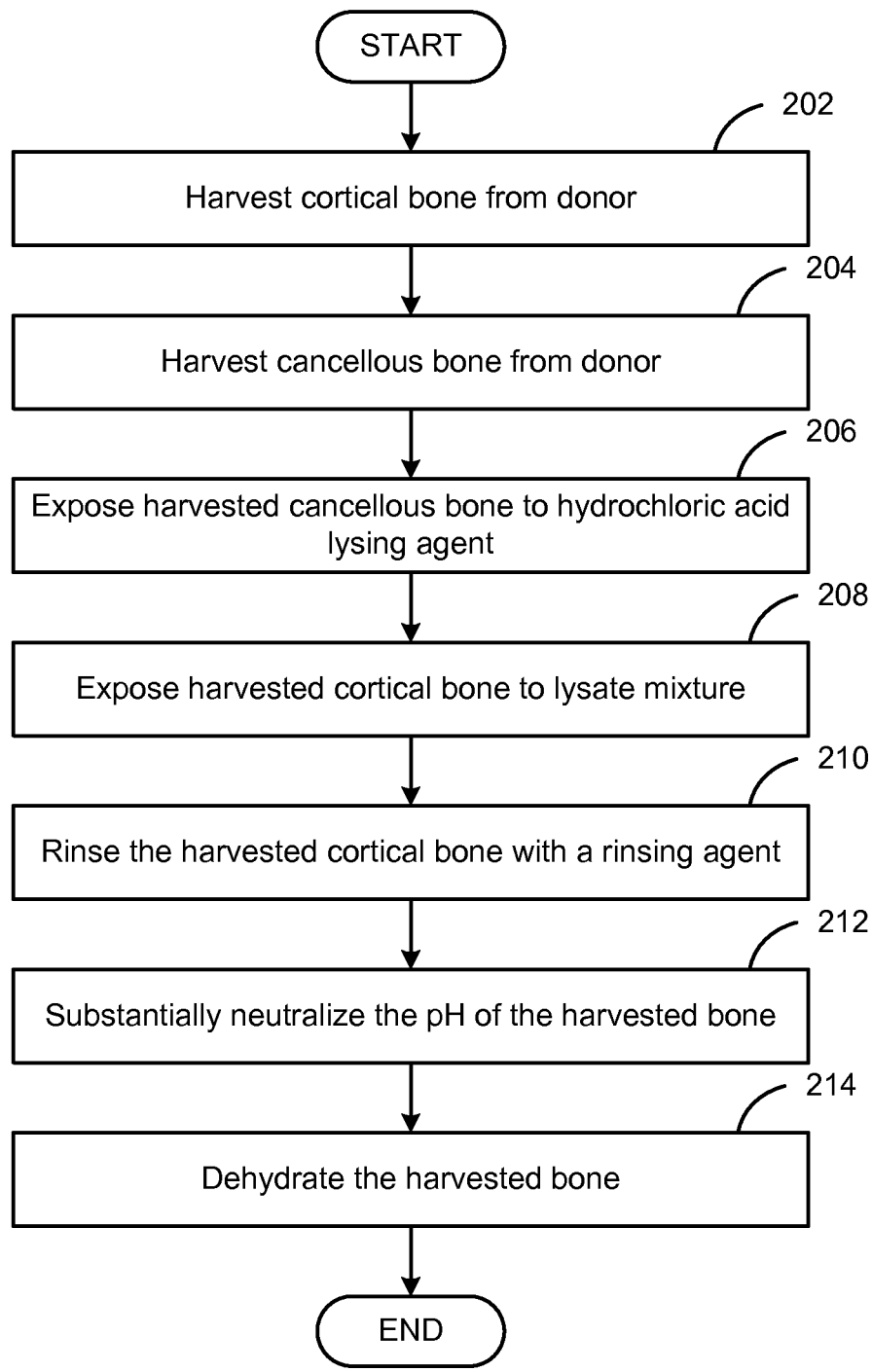
FIG. 2 is a flow diagram illustrating one embodiment in accordance with the present disclosure.

Reference is now made to FIG. 2, which depicts an alternative embodiment of the disclosure. The depicted flow diagram illustrates a method of forming an implant made from harvested cortical bone with bioactives and growth factors from harvested cancellous bone binded to the cortical bone material. In the depicted embodiment, cortical bone is harvested in box 202 from a cadaver, live donor, and/or harvested autologously from a patient. Cancellous bone is also harvested in box 204 from the same donor. The harvested cortical bone may be ground or cut to a desired shape and configuration depending on a particular application desired. The cortical bone may be cleaned and demineralized (e.g., with hydrochloric acid washes and/or treatment with citric acid) to remove its mineral content. The harvested cancellous bone may also be ground or cut to a particular shape or configuration depending on the application desired. Care may be taken to retain as much bone marrow and blood within the cancellous bone during harvest and cutting operations. Cancellous bone may have cortical bone portions such as in the iliac crest, vertebral bodies, chondyles, etc.

Accordingly, in some embodiments, depending on the application of an implant, the cancellous bone may have cortical portions removed prior to further processing. The cancellous bone is then exposed to hydrochloric acid (e.g., 0.1M-16M) as a lysing agent in box 206 to lyse cells remaining in the porous bone structure and on the bone surface. The lysing of the cells releases and/or solubilizes growth factors and bioactive materials contained in the cellular material. In contrast to the embodiment disclosed above in FIG. 1, hydrochloric acid can be employed as a lysing agent that restricts the solubilized growth factors and bioactives from binding to the cancellous bone, but they are present in the hydrochoric acid and lysate mixture. The solubilized growth factors and bioactives in the lysate mixture are then added to the cortical bone that is harvested from the same donor in box 208.

The growth factors and bioactives in the hydrochloric acid mixture readily bind to the mineralized and/or demineralized cortical bone (e.g., 1 minute-50 hour binding time). The cortical bone may be further rinsed and cleaned in box 210 after the binding to remove excess hydrochloric acid, cell fragments, lipids, and/or debris. Rinsing solutions can be water, saline, peroxides, alcohol, crystalloids, sterilizing fluids, preserving fluids, storage agents, or other fluids used in processing of allografts. The cortical bone can then undergo pH neutralization in box 212, which can be accomplished by dehydration in box 214 as is noted above in some embodiments. pH neutralization can also be accomplished by other chemical agents or physical processes as can be appreciated. Accordingly, ground particulate filler implants as well as structural cortical bone implants with increased bioactivity may be made in this manner.

Figure 3:
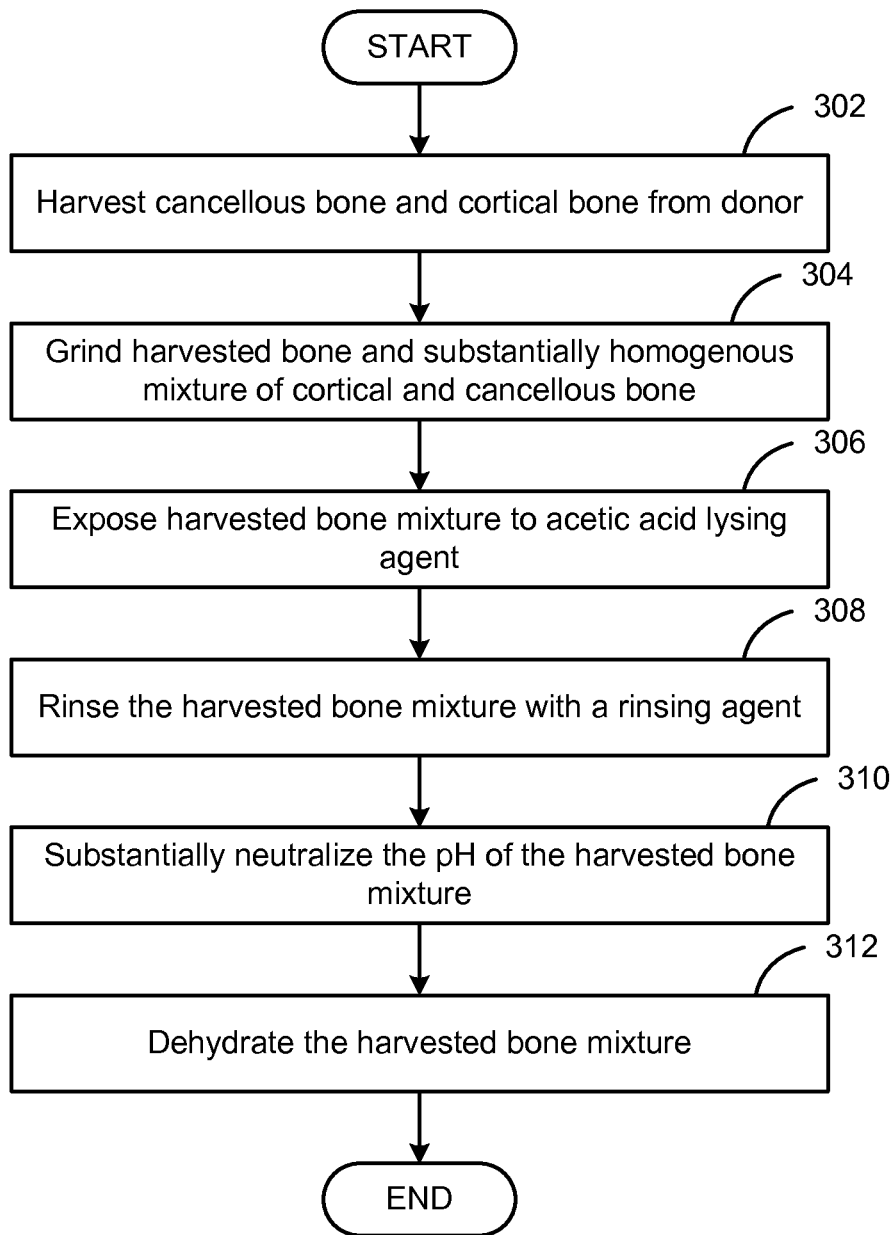
FIG. 3 is a flow diagram illustrating one embodiment in accordance with the present disclosure.

Reference is now made to FIG. 3, which depicts an alternative embodiment of the disclosure. Cortical bone and cancellous bone are harvested and/or recovered from a cadaver, live donor, or harvested autologously from a patient in box 302. If required by a particular implant application, cancellous and/or cortical bone may be ground or cut to a desired shape and configuration. Care is taken to retain as much cellular material, bone marrow, and/or blood within the bone during harvest and cutting operations. In the embodiment of FIG. 3, the harvested cancellous bone and harvested cortical bone are ground and then mixed to create a substantially homogenous mixture in box 304. Cortical bone may be demineralized using techniques of hydrochloric acid washes that are noted above prior to mixing with the cancellous bone if desired.

The cancellous and cortical bone mixture may further be homogenized by mixing with another fluid (such as water) so that the growth factors may be more homogenously distributed throughout the mixture. The solution containing bone is then exposed to acetic acid (e.g., 0.1M-17M concentrations) as a lysing agent in box 306 to lyse cells remaining in porous bone structure and on bone surface. The lysing of the cells releases and solubilizes growth factors and bioactive materials contained in the cellular material. Acetic acid also allows the solubilized bioactives to bind to the cortical and cancellous bone mixture. Further acid washes may be desired to further demineralized the bone, reduce its modulus, and/or make it more spongy. Any type of acid including acetic, hydrochloric, citric, phosphoric, etc., may be used to further demineralized the bone.

The bone may be further rinsed and cleaned in box 308 after the binding to remove excess acid, cell fragments, lipids, and/or debris. In some embodiments, the bone may be dehydrated by evaporation, vacuum drying, or lyophilization to remove any residual acetic acid and neutralize the pH of the cortical and cancellous bone mixture in boxes 310 and 312. Rinsing solutions can include water, saline, peroxides, alcohol, crystalloids, sterilizing fluids, preserving fluids, storage agents, or other fluids used in processing of allografts. Accordingly, ground particulate filler implants as well as structural corticocancellous bone implants with increased bioactivity may be made in this manner.

Figure 4:
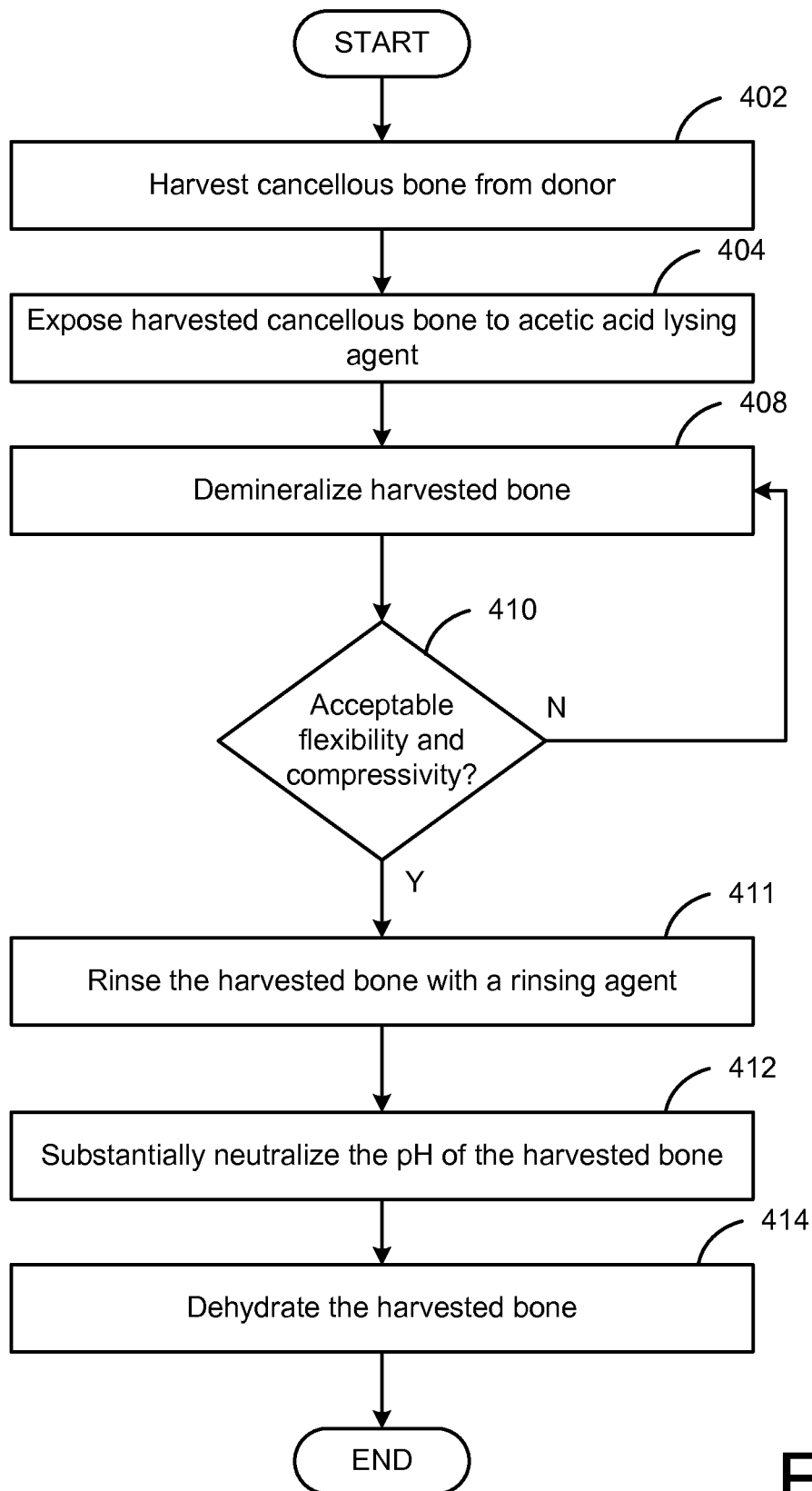
FIG. 4 is a flow diagram illustrating one embodiment in accordance with the present disclosure.

Reference is now made to FIG. 4, which depicts an alternative embodiment of the disclosure. Cancellous bone is recovered from a cadaver, live donor, or harvested autologously from a patient in box 402. If required by a particular implant application, the harvested cancellous bone may be ground or cut to a desired shape and configuration. Care may be taken to retain as much cellular material, bone marrow, and/or blood within the bone during harvest and cutting operations. Cancellous bone may have cortical bone portions such as in the iliac crest, vertebral bodies, chondyles, etc. Accordingly, cortical portions of cancellous bone may be removed from the cancellous bone. The cancellous bone can then be exposed to acetic acid (e.g., 0.1M-17M) as a lysing agent in box 404 to lyse cells remaining in porous bone structure and on bone surface. The lysing of the cells releases and solubilizes growth factors and bioactive materials contained in the cellular material. Acetic acid also allows the solubilized bioactives to bind to the bone. The cancellous bone may be further demineralized in box 408 using at least one demineralization wash using any acid, including, but not limited to, acetic, hydrochloric, citric, phosphoric, etc., to alter the mechanical properties of the bone and remove mineral content.

A compression test may be performed between demineralization washes to determine the whether the level of flexibility and compressivity of the bone is acceptable for a given application in box 410. If the bone is too rigid for a desired application, further demineralization washes may be performed. Once the desired flexibility is achieved, the bone may be further rinsed and cleaned in box 411 after the binding to remove excess acid, cell fragments, lipids, or depris. In some embodiments, the bone may be dehydrated by evaporation, vacuum drying, or lyophilization to residual any residual acetic acid and bring the implant to a more neutral pH in boxes 412 and 414. It should be appreciated that pH neutralization can be accomplished by chemical agents or physical processes other than by dehydration. Rinsing solutions can be water, saline, peroxides, alcohol, crystalloids, sterilizing fluids, preserving fluids, storage agents, etc., or other fluids used in processing of allografts. Accordingly, ground particulate filler implants as well as structural but flexible/compressible cancellous bone implants with increased bioactivity may be made in this manner.

Figure 5:
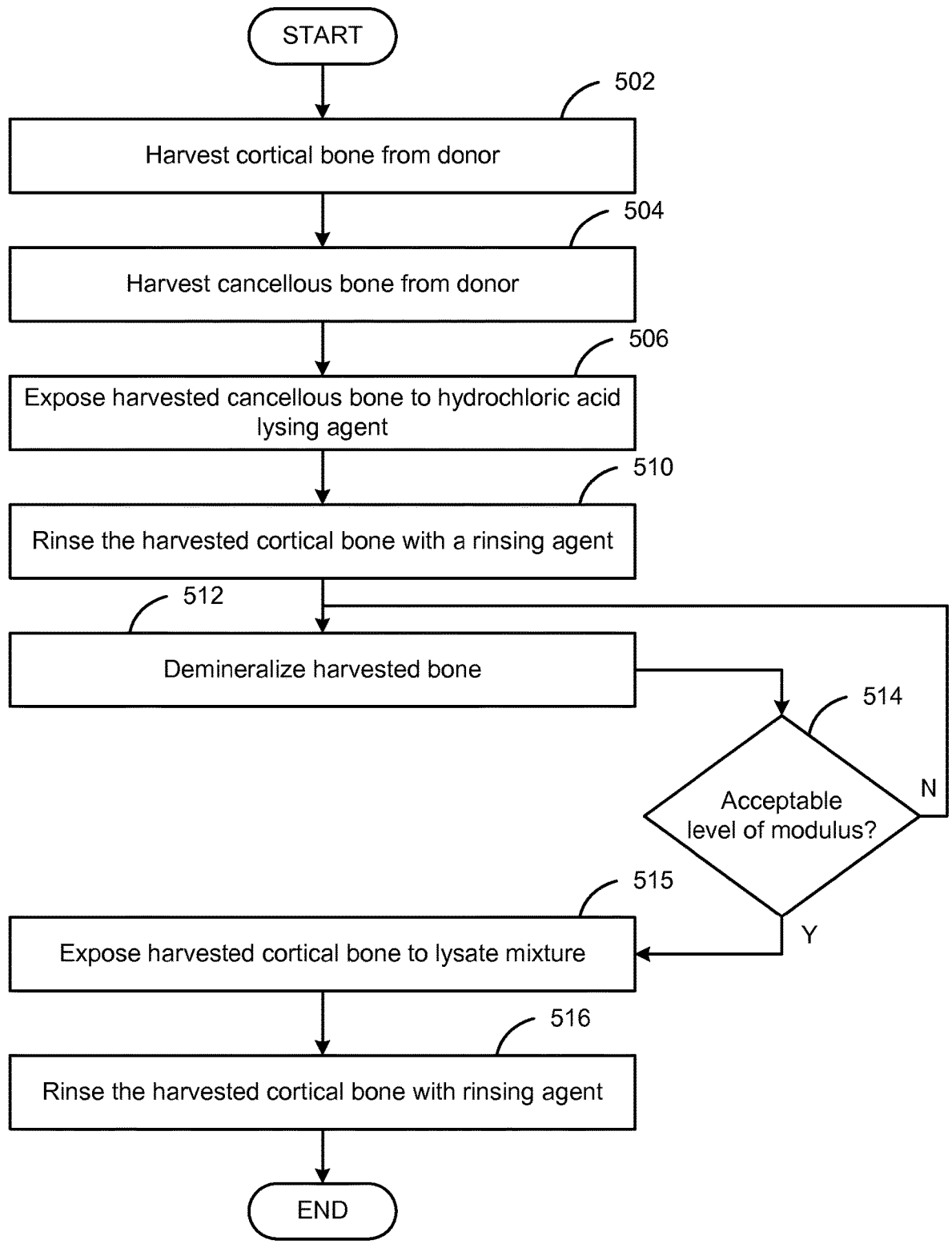
FIG. 5 is a flow diagram illustrating one embodiment in accordance with the present disclosure.

Reference is now made to FIG. 5, which depicts an alternative embodiment of the disclosure. Cortical bone is harvested from a cadaver, live donor, or harvested autologously from a patient in box 502. Depending on the application of the implant, cortical bone may be ground or cut to a desired shape and configuration. Accordingly, cancellous bone is also harvested from the same donor as the cortical bone in box 504. The cancellous bone may be ground or cut to a particular shape or configuration depending on the application of the implant. Care may be taken to retain as much cellular material, bone marrow, and/or blood within the cancellous bone during harvest and cutting operations. Cancellous bone may have cortical bone portions such as in the iliac crest, vertebral bodies, chondyles, etc. Accordingly, the cancellous bone may have cortical portions removed prior to further processing. The cancellous bone is exposed to a lysing agent, such as, but not limited to, hydrochloric acid in box 506 to lyse cells remaining in porous bone structure and on bone surface.

The harvested cortical bone may be cleaned and demineralized in boxes 510 and box 512 to remove its mineral content, including, but not limited to, calcium salts. This demineralization process may involve soaking in acid and/or cyclic vacuum perfusion of acid into the pores of the bone.

Employing a vacuum assisted cyclic method of demineralization may, as a non-limiting example, decrease required demineralization time from one to fifty-nine minutes. A vacuum assisted cyclic demineralization cycle can facilitate substantially uniform removal of calcium minerals throughout the implant rather than just on the surface. Non-uniform removal of calcium minerals may occur if the demineralization step is performed by soaking the cortical bone in acid. Non-uniform calcium mineral removal can result in varying calcium concentrations gradient throughout different portions of the implant.

Employing vacuum assisted cyclic demineralization can result in a more homogenous calcium concentration relative to soaking the sample in acid, resulting in stronger implants with better toughness and resilience. Additionally, this process can be used to reduce the modulus of bone to better match the natural mechanical properties found at the patient's surgical implantation site. This can be advantageous in osteoporotic, osteopenic patients, or patients with low bone density or bone mineral density. Also, this homogenous reduced modulus is advantageous in surgical sites where the implantation site is decorticated. Uniform calcium mineral removal can also reduce subsidence rates in spinal fusions. Also, better growth factor retention may be found within cortical bone using vacuum assisted cyclic demineralization.

If it is determined in box 514 that the level of modulus of the cortical bone is acceptable, this reduced modulus cortical or corticocancellous bone can also be made with binded growth factors and/or bioactive materials. The lysing of the cells of the harvested cancellous bone releases and solubilizes growth factors and bioactive materials contained in the cellular material. Hydrochloric acid also restricts the solubilized bioactives and growth factors from binding to the cancellous. The solubilized growth factors and bioactives in the hydrochloric acid are added to the cortical bone that is harvested from the same donor in box 515. The growth factors and bioactives readily bind to the mineralized or demineralized cortical bone.

The bone may be further rinsed and cleaned after the binding in box 516 to remove excess hydrochloric acid, cell fragments, lipids, and/or debris, etc. Rinsing solutions can be water, saline, peroxides, alcohol, crystalloids, sterilizing fluids, preserving fluids, storage agents, or other fluids used in processing of allografts. Additionally, the implant can be made flexible before or after binding bioactives and/or growth factors if the implant is further demineralized. Accordingly, reduced modulus structural bone implants with increased bioactivity may be made in this manner.

Figure 6:
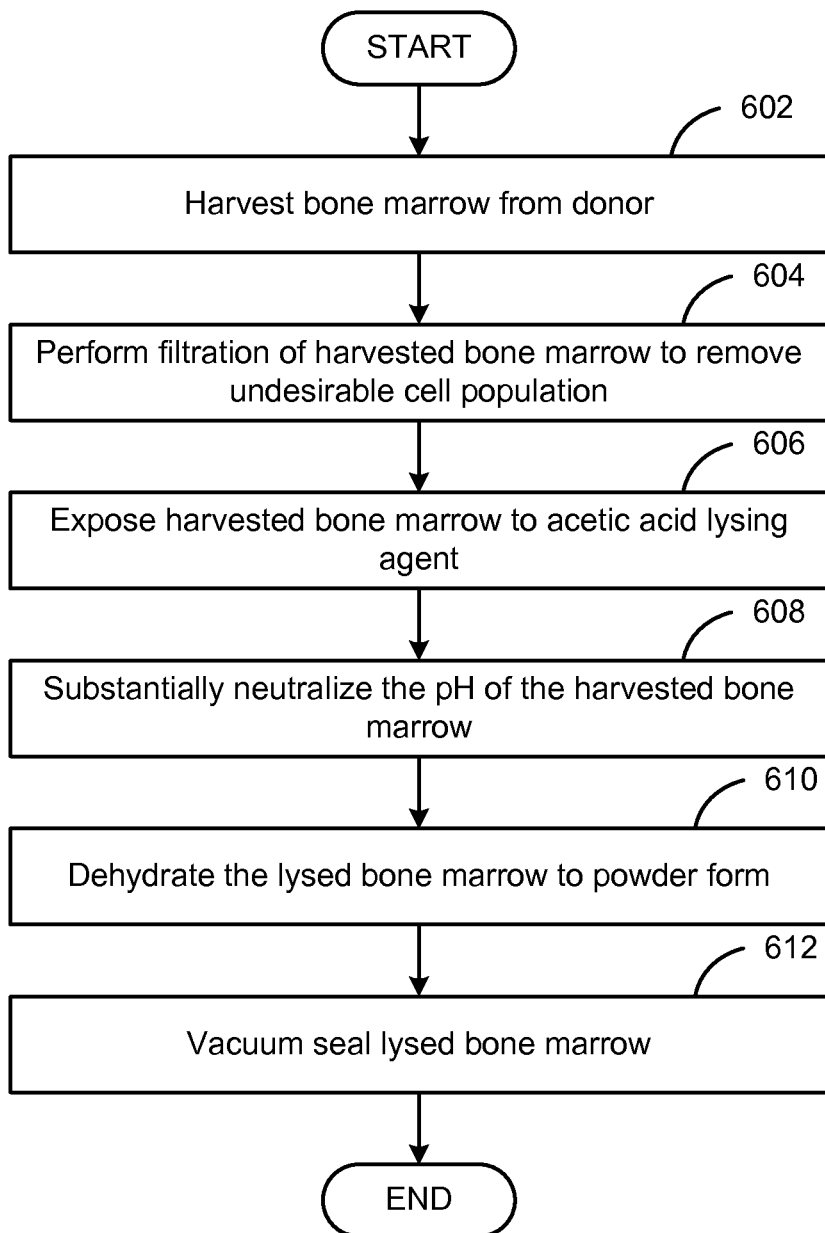
FIG. 6 is a flow diagram illustrating one embodiment in accordance with the present disclosure.

Reference is now made to FIG. 6, which depicts an alternative embodiment of the disclosure. Bone marrow is harvested from a cadaver, live donor, or harvested autologously from a patient in box 602. If a cadaver donor is used, a higher volume of marrow may be obtained by harvesting the marrow before any bone sectioning is done. In some embodiments, using a cannulated drill attached to a vacuum line to harvest marrow would also increase the yield of bone marrow from a cadaver donor. The tip of the cannulated drill breaks apart within the cancellous bone, allowing the vacuum to pull marrow through the cannula into a collection chamber.

Harvesting marrow from a living donor prior to the donor being removed from life support can also be employed as a marrow harvesting technique, because as the marrow is removed, blood flow caused by physiological circulation flushes additional bone marrow material into the area for further aspiration. After marrow has been harvested, particular cell types (such as mesenchymal stem cells, osteoblasts, osteocytes, or other progenitor cells) may be concentrated by filtration, centrifugation, magnetic bead binding, fluorescence activated cell sorting (FACS), and/or other cell sorting or concentration techniques as can be appreciated to increase the cell concentration, fractionate cell types, or eliminate particular cell types from the solution in box 604. Once, the desired cell population is obtained, it may be exposed to a lysis technique previously described, such as exposure to acetic acid in box 606.

Once acetic acid is added to the cells, they are given time to lyse and the growth factors and other bioactives are solubilized. The solution can be centrifuged or filtered to eliminated any cell fragments or cellular debris. The solution may undergo a second filtration step to remove other solid precipitates such as precipitated hemoglobin. The solution may undergo a third filtration step to concentrate the growth factors and other bioactives in the solution. The solution is then dehydrated by methods previously described, such as lyophilization. The solution is reduced to a water soluble powder in box 610 and may be sealed under vacuum to increase shelf-life in box 612. The solution can also be frozen to increase shelf life. This powder can be rich in a number or bioactive molecules and/or growth factors including, but not limited to, BMP-2, VEGF, aFGF, FGF-6, TGF-B1, and others as can be appreciated.

Figure 7:
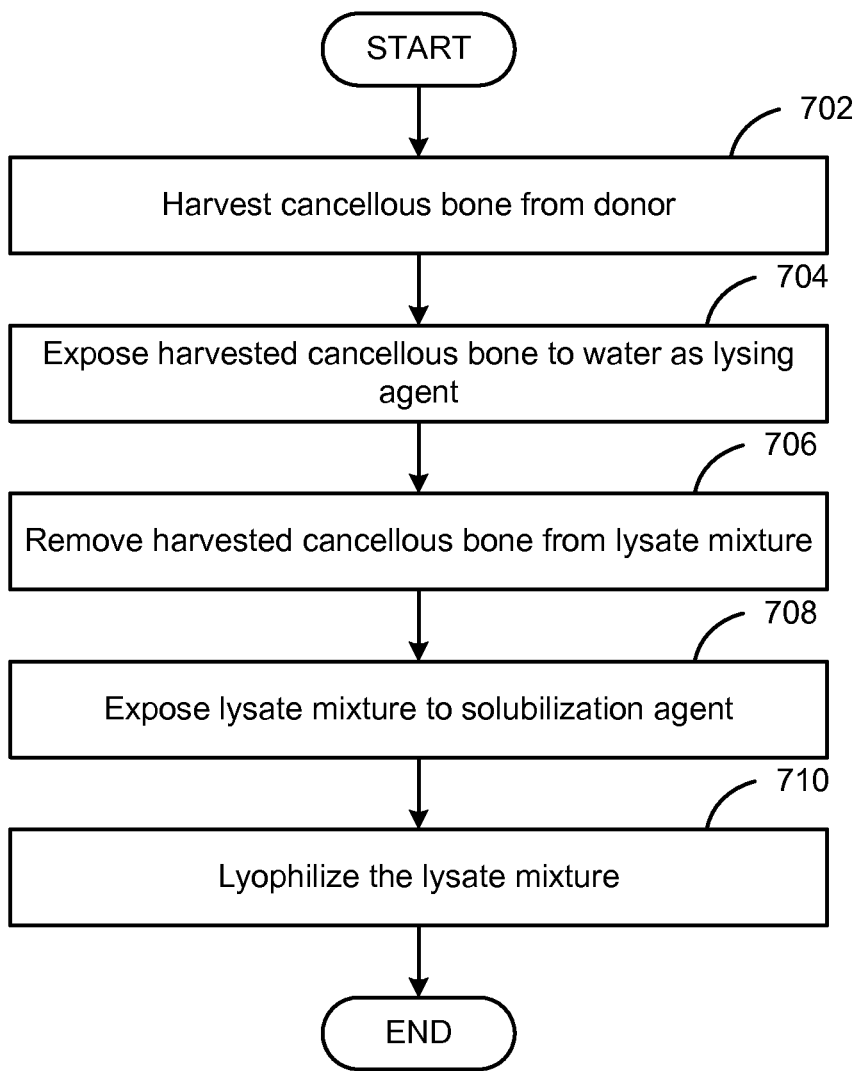
FIG. 7 is a flow diagram illustrating one embodiment in accordance with the present disclosure.

Reference is now made to FIG. 7, which depicts an alternative embodiment of the disclosure. In the depicted embodiment, cancellous bone is recovered from a cadaver, live donor, or harvested autologously from a patient in box 702. If required by a particular implant application, the harvested cancellous bone may be ground or cut to a desired shape and configuration. Care may be taken to retain as much bone marrow and blood within the bone during harvest and cutting operations. Cancellous bone may have cortical bone portions such as in the iliac crest, vertebral bodies, chondyles, etc. Accordingly, the cancellous bone may have cortical portions removed prior to further processing. The harvested cancellous bone is then exposed to a lysing agent, such as water, to lyse the cells contained in the cancellous bone in box 704. If a particular anticoagulant, such as heparin, is used as a lysing agent, the growth factors released by lysing the cells will be solubilized in solution. If no anticoagulant is used or if a different anticoagulant is used, such as sodium citrate, the cells will be lysed and release growth factors, but they will not be fully solubilized in the fluid.

In this case, the bone is then removed from the fluid in box 706 and a solubilization agent, such as an acid, is added to the fluid to solubilize the growth factors and other bioactives in box 708. Once the growth factors and other bioactives have been solubilized, the fluid may be neutralized and/or lyophilized in box 710. If acetic acid was used as the solubilizer, neutralization may be unnecessary as a substantial amount of acetic acid will vaporize during lyophilization. Alternatively, other lysing agents and solubilizers could be used to lyse the cells and solubilize the growth factors, preventing the growth factors and bioactive materials from binding to the cancellous bone from which the cells were harvested.

Figure 8:
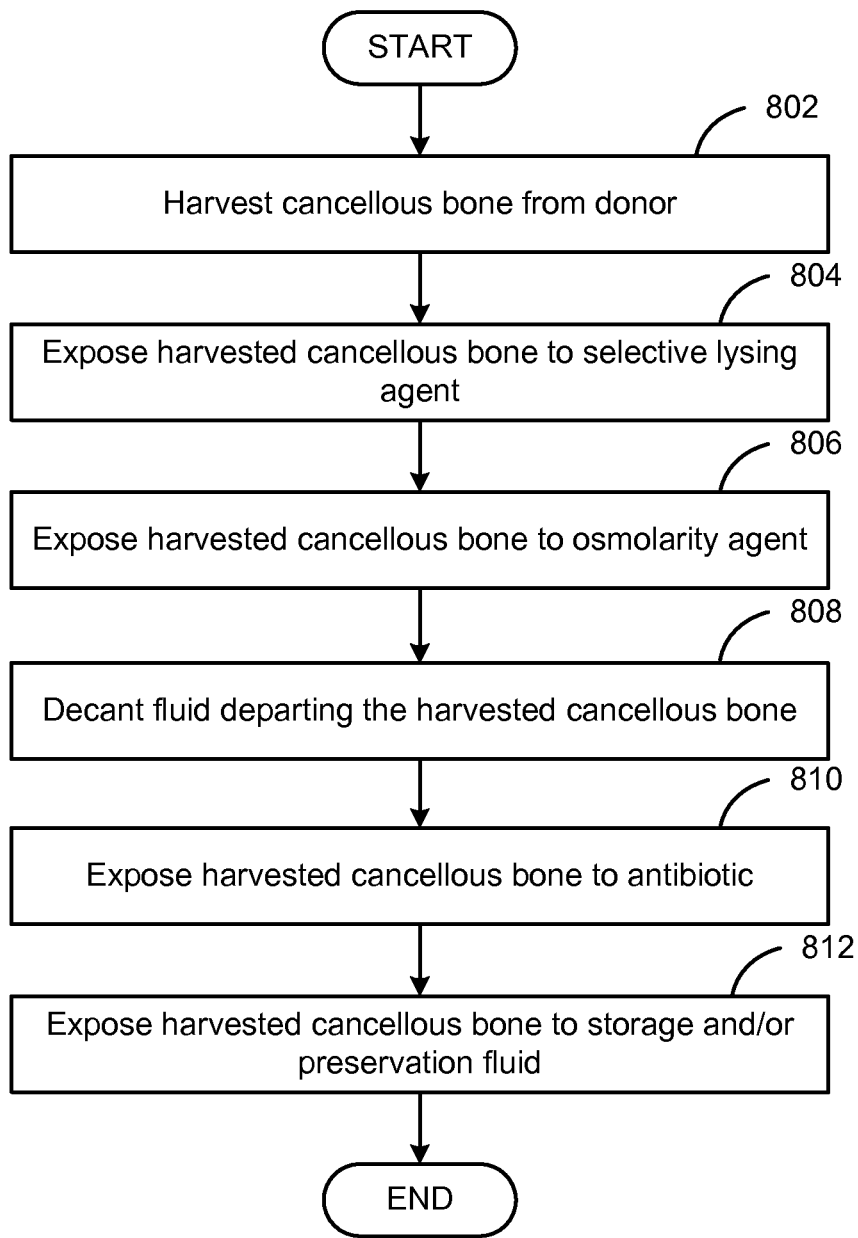
FIG. 8 is a flow diagram illustrating one embodiment in accordance with the present disclosure.

Reference is now made to FIG. 8, which depicts an alternative embodiment of the disclosure. In the depicted embodiment, cancellous bone is recovered from a cadaver, live donor, or harvested autologously from a patient in box 802. If required by a particular implant application, cancellous bone may be ground or cut to a desired shape and configuration. Care may be taken to retain as much bone marrow and blood within the bone during harvest and cutting operations. Cancellous bone may have cortical bone portions such as in the iliac crest, vertebral bodies, chondyles, etc. Accordingly, cortical portions of the harvested cancellous bone may be removed. The harvested cancellous bone is exposed to water to selectively lyse undesired cells types such as red blood cells, white blood cells, etc in box 804. In some embodiments, ratios of bone to water from 1 part bone to 1 part water and ranging to 1 part bone to 200 parts water can be employed. Any remaining viable cells that are not attached to the bone may be rinsed away in this fashion. Additionally, using a weak lysing agent (such as less then 1M acetic acid) may result in binding solubilized growth factors to the bone but still retaining viable progenitor cells attached to the bone.

The desired cells, such as mesenchymal stem cells, bone marrow stromal cells, progenitor cells, etc., remain viable in porous bone structure and on bone surface. Other mechanical lysing techniques previously described, such as sonication, stirring induced shear, thermoslysis, etc., may be used in conjunction with the water bath to facilitate lysing of cellular material. After a lysing time (e.g., 1 minute-50 hours) has elapsed, saline is added to return osmolarity of the solution to physiological levels (e.g., approximately 0.9% salt) in box 806. After the solution is returned to isotonic conditions, the fluid is decanted leaving the bone in box 808. The effective rinse also facilitates removal of undesired cells unattached to the cancellous bone and discards them in the decanting step.

Antibiotics may be applied to the bone in box 810 to help with decreasing bioburden levels. Alternatively, in some embodiments antibiotics can be administered to the harvested cancellous bone prior to the lysing step. Some antibiotics that may be used include gentamicin, vancomycin, amphotericin, other antibiotics previously mentioned or as can be appreciated, or various antibiotics that can be used to reduce bioburden in allograft tissues. After the reduction of bioburden, the bone may be exposed to storage or preservation fluids such as DMEM, DMSO, sucrose, mannitol, glucose, etc., in box 812. The bone is then frozen until thawed for use in a surgical procedure to repair a skeletal defect. In some embodiments, the bone can be frozen at temperatures at or below −40 C.

Figure 9:
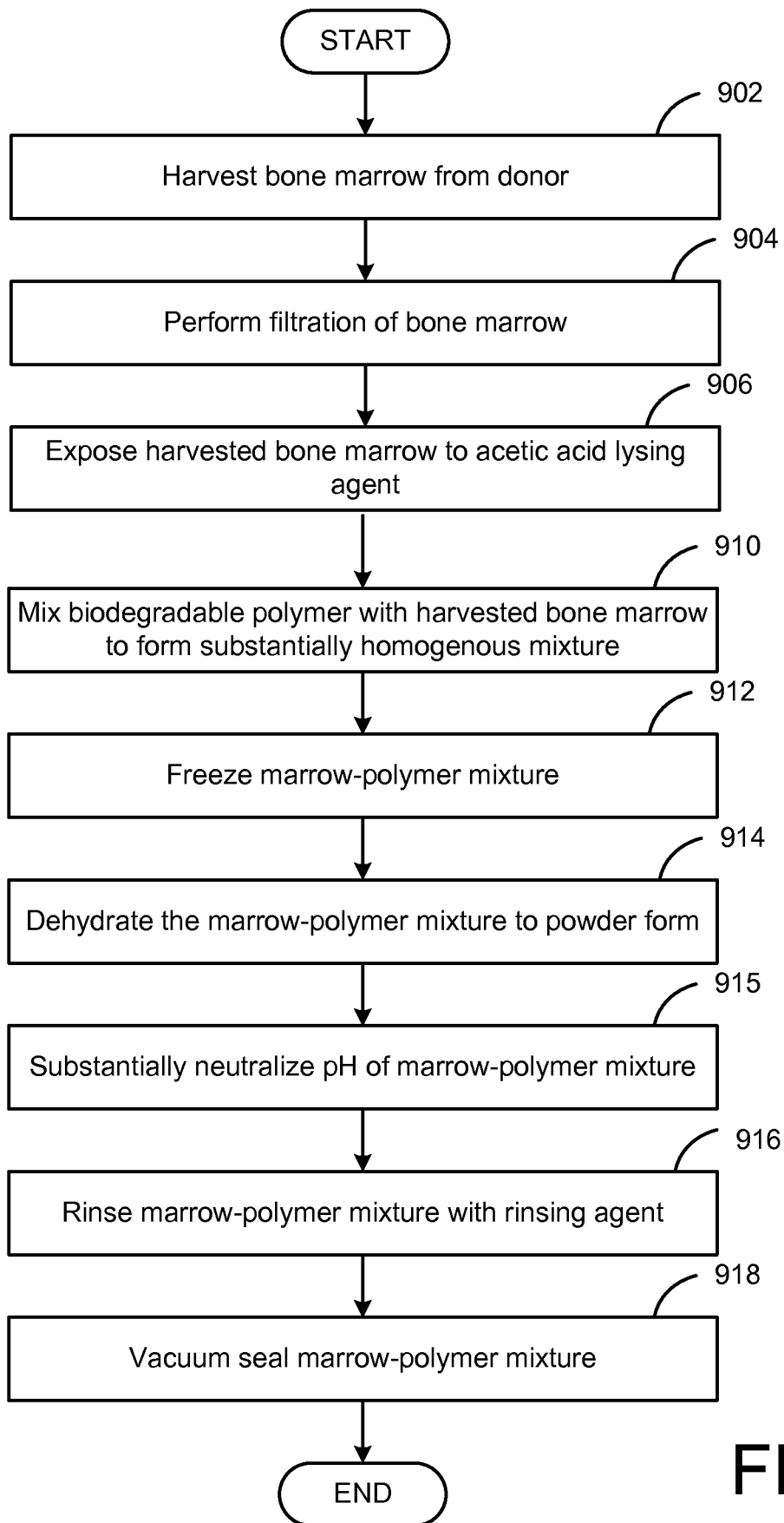
FIG. 9 is a flow diagram illustrating one embodiment in accordance with the present disclosure.

Reference is now made to FIG. 9, which depicts an alternative embodiment of the disclosure. In the depicted embodiment, the growth factors and bioactives obtained in the embodiments described above with reference to FIGS. 6 and/or 7 (as a non-limiting example) may be added to a biodegradable or resorbable polymer prior to dehydration. Accordingly, bone marrow harvested in box 902 can be subjected to at least one filtration process in box 904 as described above with reference to FIG. 6. The harvested bone marrow can be subjected to a lysing agent in box 906 as also described above.

In this embodiment, the growth factors and bioactives are harvested as previously described and added to a polymer with a common solvent, such as an acid. The biodegradable polymer may be a protein or polysaccharide, such as collagen, hyaluronan, chitosan, gelatin, etc., and combinations of two or more polymers. After the growth factors and bioactives are added to the polymer, it is mixed to obtain a substantially homogenous solution in box 910. Any bubbles or impurities may then be removed from the substantially homogenous solution. If other materials (such as, but not limited to, calcium phosphate, demineralized bone, hydroxyapatite, heparin, chondroitin sulfate, etc.) are desired to be embedded into the implant for growth factor attachment, degradation by products, and/or mechanical reinforcement, they can also be added to the mixture.

The mixture is frozen in box 912 at a temperature that can range, in some embodiments, from −200 C to 0 C, to nucleate the water contained in the mixture into ice as well as condense the polymer/bioactive mixture into a porous structure. The mixture can be frozen in any geometry including, spherical, cylindrical, rectangular, in sheet form, tube form, etc. The implant will tend to retain this shape with its shape memory properties of the polymer is given space to expand in vivo. Temperatures can be increased to create larger pores or decreased to create small pores. Pores can be made directional by locating the cold temperature source substantially perpendicularly to the desired direction of the pores. Once the mixture is frozen at the desired temperature and pore direction, the implant is lyophilized and/or dehydrated in box 914 to substantially eliminate the water contained within it. If acetic acid or another volatile substance was used as the solvent, that solvent will also be substantially eliminated by lyophilization.

After the lyophilization cycle is complete, the scaffold may be substantially neutralized in ethanol, saline, base, or buffer depending on the solvent used as a lysing agent in box 915. In the case of an acetic acid solvent, the lyophilized implant may be rinsed in ethanol followed by saline or other rinsing agent in box 916. After the saline rinse, the implant may be rinsed free of salts with water and vacuum dried or lyophilized to extend shelf-life. The dehydrated implants may be packaged under vacuum or sealed in vacuum sealed vials in box 918. The implant can also be compressed prior to freezing and lyophilization or after neutralization and lyophilization to create a compacted scaffold that expands when exposed to fluid. Upon exposure to fluid, such an implant expands to substantially to approximately the original scaffold size. Delayed expansion may be achieved by compressing the neutralized scaffold and drying without freezing.

Figure 10:
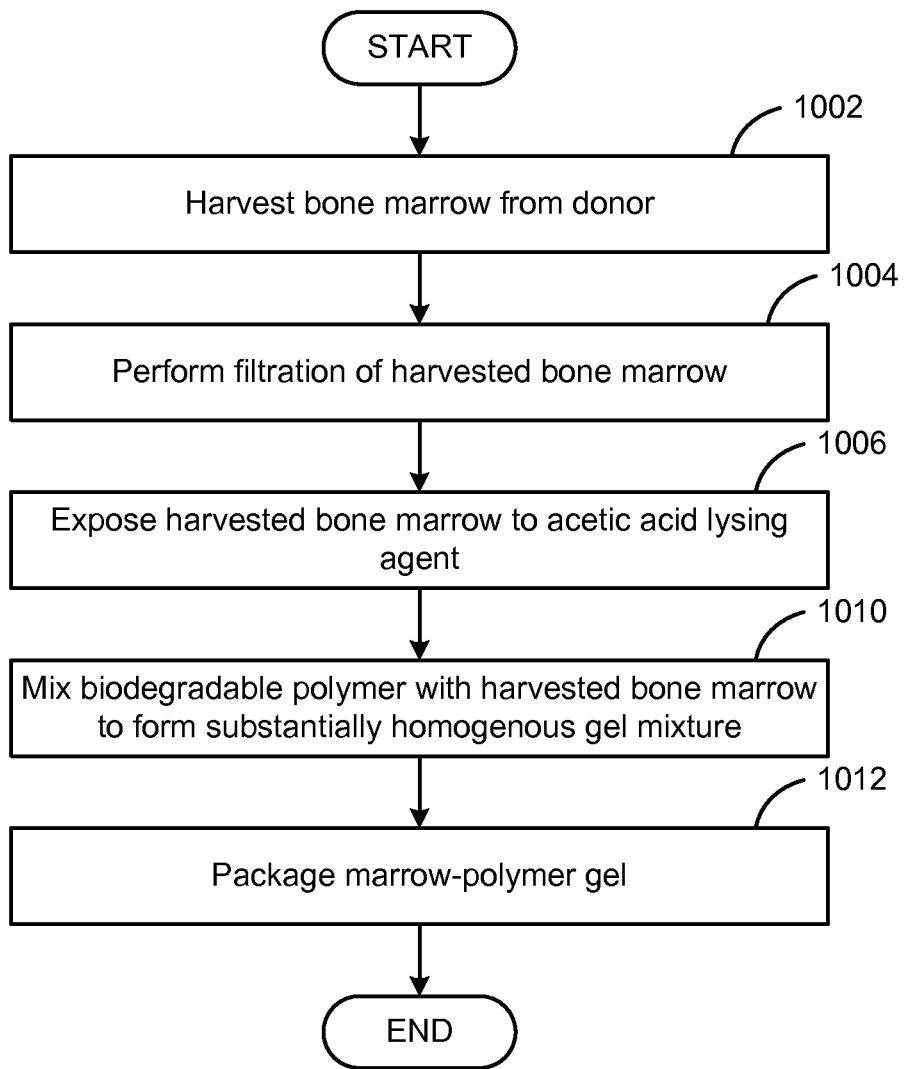
FIG. 10 is a flow diagram illustrating one embodiment in accordance with the present disclosure.

Reference is now made to FIG. 10, which depicts an alternative embodiment of the disclosure. In the depicted embodiment, the growth factors and/or bioactives obtained in the embodiments discussed with reference FIGS. 6 and 7 (as a non-limiting example) may be added to a biodegradable or resorbable polymer to create a flowable fluid and/or gel. In this embodiment, the growth factors and bioactives are harvested as previously described and added to a polymer with a common solvent, such as an acid. Accordingly, bone marrow harvested in box 1002 can be subjected to at least one filtration process in box 1004 as described above with reference to FIG. 6. The harvested bone marrow can be subjected to a lysing agent in box 1006 as also described above.

The biodegradable polymer may be a protein or polysaccharide, such as collagen, hyaluronan, chitosan, gelatin, etc., and combinations of two or more polymers. After the growth factors and bioactives are added to the polymer, it is mixed to obtain a substantially homogenous solution in box 1010. Any bubbles or impurities may be removed. If other materials (including, but not limited to, calcium phosphate, demineralized bone, hydroxyapatite, heparin, chondroitin sulfate, etc.) are desired to be embedded into the implant for growth factor attachment, degradation by products, and/or mechanical reinforcement, they can also be added to the mixture.

A lysing agent can be chosen that is well tolerated by the body. For example, the growth factors and bioactives can be added to chitosan and in an acetic acid solution (0.01M-17M). Demineralized bone can also be added to the solution. The solution is mixed, and bubbles can be removed by applying vacuum or centrifugation. The gel can be packaged in syringes and either frozen and/or kept at ambient temperature in box 1012. Once injected and/or implanted into the body, the gel binds to tissue. Physiological fluids may buffer the gel to neutralize the pH and cause the gel to solidify in situ. Once the gel solidifies, the desired therapeutic implant remains in the intended surgical site and minimizes migration.

Figure 11:
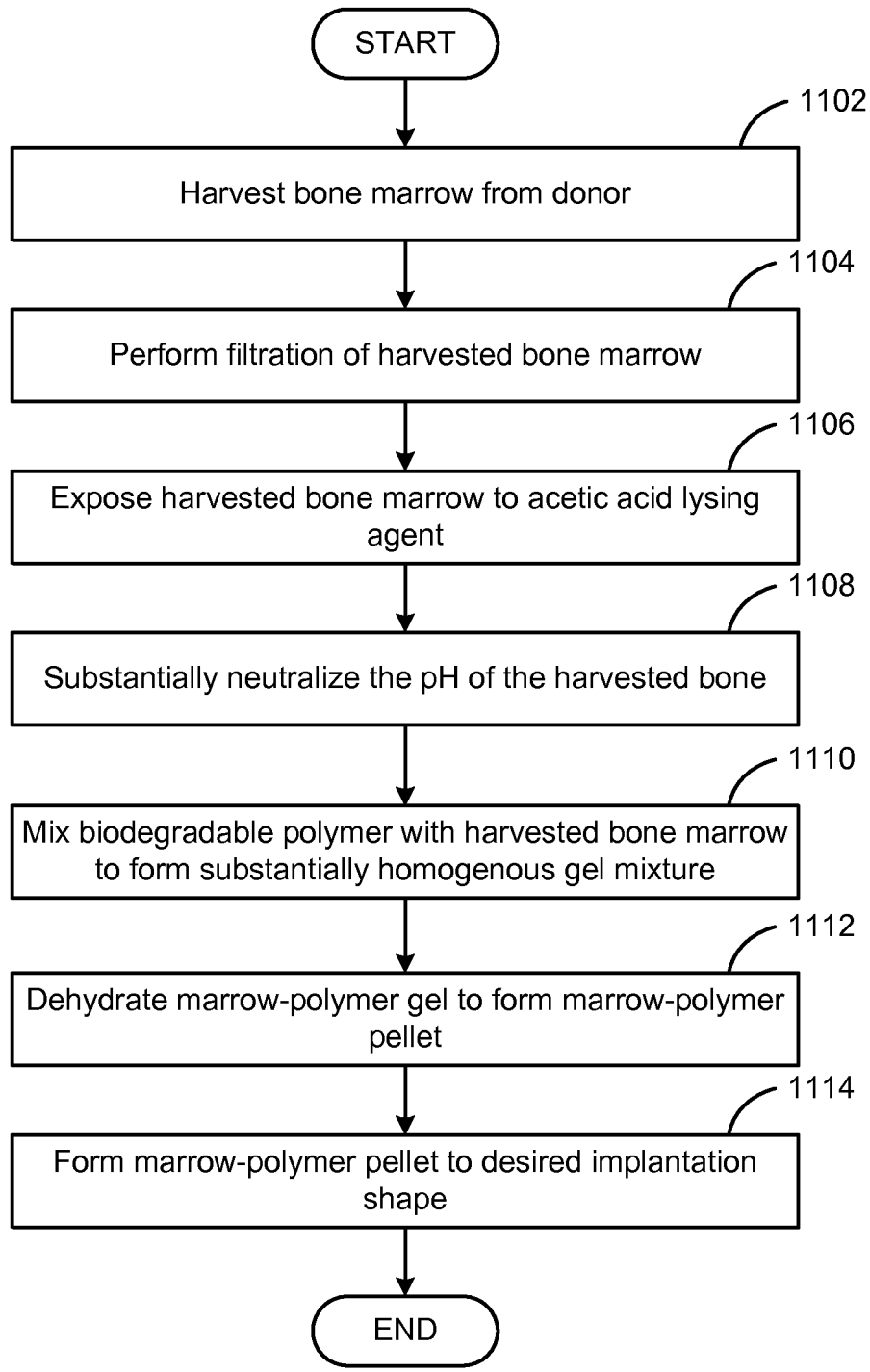
FIG. 11 is a flow diagram illustrating one embodiment in accordance with the present disclosure.

Reference is now made to FIG. 11, which depicts an alternative embodiment of the disclosure. A gel obtained as described in the above embodiment discussed with reference to FIG. 10 may be dehydrated using techniques such as vacuum drying, solvent evaporation, etc., to reduce the gel into a semi-rigid film and/or pellet. Accordingly, bone marrow harvested in box 1102 can be subjected to at least one filtration process in box 1104 as described above with reference to FIG. 6. The harvested bone marrow can be subjected to a lysing agent in box 1106 as also described above.

The gel is dehydrated as described above in box 1112. The pellets may be ground further or cut into the desired particle size depending on a desired implant application in box 1114. Once exposed to fluid and implanted into the surgical site, the pellets and/or powder resulting from ground pellets form a cohesive putty that can also bind to tissue. This binding property keeps the putty substantially in place at the surgical site when implanted. This putty can be used as a bioactive surgical adhesive. The application of such a putty may also be advantageous when used with autologous materials used in surgical procedures, such as autograft bone used in spinal fusion procedures, because it may be beneficial to help keep the autograft in a cohesive mass and minimize migration.

Although the flowcharts depicted in the included drawings show a specific order of execution of the various steps, it is understood that the order of execution may differ from that which is depicted. For example, the order of execution of two or more blocks may be scrambled relative to the order shown. Also, two or more blocks shown in succession may be executed concurrently or with partial concurrence. It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Therefore, the following is claimed:

1. A bone implant prepared by a process comprising the steps of:
   harvesting bone material from a donor;
   exposing the harvested bone material to a lysing agent, the lysing agent configured to release native bone morphogenetic proteins from the harvested bone material;
   allowing the released native bone morphogenetic proteins to bind to the harvested bone material;
   demineralizing the harvested bone with bone morphogenetic proteins bound thereto with hydrochloric acid;
   rinsing the harvested bone material;
   wherein the rinsed bone comprises a bone implant comprising demineralized bone and bone morphogenetic proteins derived from the bone.

2. The bone implant of claim 1, wherein the harvested bone material comprises bone marrow.

3. The bone implant of claim 1, wherein the harvested bone comprises cortical or cancellous bone.

4. The bone implant of claim 1, wherein the bone comprises ground particulate.

5. The bone implant of claim 1, wherein the implant further comprises antibiotics.

6. The bone implant of claim 1, having reduced bone modulus.

* * * * *